(12) United States Patent
Yue et al.

(10) Patent No.: US 12,397,138 B2
(45) Date of Patent: Aug. 26, 2025

(54) BALLOON DILATION CATHETER, BALLOON AND PREPARATION METHOD THEREFOR

(71) Applicant: SHANGHAI MICROPORT CARDIOFLOW MEDTECH CO., LTD., Shanghai (CN)

(72) Inventors: Bin Yue, Shanghai (CN); Jingwei Jia, Shanghai (CN); Guoming Chen, Shanghai (CN); Yu Li, Shanghai (CN)

(73) Assignee: SHANGHAI MICROPORT CARDIOFLOW MEDTECH CO., LTD., Shanghai (CN)

( * ) Notice: Subject to any disclaimer, the term of this patent is extended or adjusted under 35 U.S.C. 154(b) by 1123 days.

(21) Appl. No.: 17/291,530

(22) PCT Filed: Nov. 5, 2019

(86) PCT No.: PCT/CN2019/115699
§ 371 (c)(1),
(2) Date: May 5, 2021

(87) PCT Pub. No.: WO2020/094001
PCT Pub. Date: May 14, 2020

(65) Prior Publication Data
US 2022/0016400 A1 Jan. 20, 2022

(30) Foreign Application Priority Data
Nov. 5, 2018 (CN) .......................... 201811317928.7

(51) Int. Cl.
*A61M 25/10* (2013.01)
*A61L 29/04* (2006.01)
*A61L 29/06* (2006.01)

(52) U.S. Cl.
CPC ....... *A61M 25/1029* (2013.01); *A61L 29/049* (2013.01); *A61L 29/06* (2013.01);
(Continued)

(58) Field of Classification Search
CPC ............ A61M 25/1029; A61M 29/049; A61M 29/06; A61M 2025/1075; A61M 2025/1079
See application file for complete search history.

(56) References Cited

U.S. PATENT DOCUMENTS

| | | |
|---|---|---|
| 2013/0085519 A1 | 4/2013 | Kiminami |
| 2014/0276585 A1 | 9/2014 | Gianotti |
| 2016/0058982 A1 | 3/2016 | Aggerholm et al. |

FOREIGN PATENT DOCUMENTS

| | | |
|---|---|---|
| CN | 1162325 A | 10/1997 |
| CN | 1492899 A | 4/2004 |

(Continued)

*Primary Examiner* — Michael C Miggins
(74) *Attorney, Agent, or Firm* — Muncy, Geissler, Olds & Lowe, P.C.

(57) ABSTRACT

A balloon dilation catheter, a balloon (10) and preparation method therefor. The balloon (10) is prepared by co-mixing at least two of L25, TR55, TR90, and TR70, and has high puncture resistance and low compliance with respect to a balloon (10) made of a single nylon material. The balloon (10) is preferably a hollow multilayer structure, and the puncture resistance of the balloon (10) can be further improved and the compliance can be further reduced with respect to a single-layer structure.

14 Claims, 1 Drawing Sheet

(52) U.S. Cl.
CPC ............... *A61M 2025/1075* (2013.01); *A61M 2025/1079* (2013.01); *A61M 2207/00* (2013.01)

(56) References Cited

FOREIGN PATENT DOCUMENTS

| | | |
|---|---|---|
| CN | 101218301 A | 7/2008 |
| CN | 101610798 A | 12/2009 |
| CN | 102793962 A | 11/2012 |
| CN | 102883753 A | 1/2013 |
| CN | 103249435 A | 8/2013 |
| CN | 103282075 A | 9/2013 |
| CN | 103298517 A | 9/2013 |
| CN | 104135958 A | 11/2014 |
| CN | 104271193 A | 1/2015 |
| CN | 104411263 A | 3/2015 |
| CN | 104582778 A | 4/2015 |
| CN | 104955515 A | 9/2015 |
| CN | 105599284 A | 5/2016 |
| CN | 105727375 A | 7/2016 |
| CN | 106178231 A | 12/2016 |
| CN | 106730252 A | 5/2017 |
| CN | 107198813 A | 9/2017 |
| CN | 107261301 A | 10/2017 |
| CN | 107400323 A | 11/2017 |
| CN | 107635593 A | 1/2018 |
| CN | 107793603 A | 3/2018 |
| CN | 107823721 A | 3/2018 |
| CN | 107841092 A | 3/2018 |
| CN | 107847713 A | 3/2018 |
| CN | 108211093 A | 6/2018 |
| EP | 2919847 B1 * | 7/2019 ............. A61L 29/04 |
| WO | WO2018033920 A1 | 2/2018 |

* cited by examiner

BALLOON DILATION CATHETER, BALLOON AND PREPARATION METHOD THEREFOR

TECHNICAL FIELD

The present application relates to the field of medical instruments and, in particular, to a balloon dilatation catheter, a balloon and a preparation method thereof.

BACKGROUND

Since its first successful application by Inoue in 1984, percutaneous balloon valvuloplasty (PBV) has been considered important for the treatments of heart valve diseases. Due to a wide range of advantages including less trauma, safety, and proved curative effect, PBV has replaced open heart valvulotomy/dissection to some extent. Valve balloons are suitable for patients with severe calcified aortic stenosis, who are contraindicated for surgical treatment or associated with a high surgical risk. A valve balloon can widen and dredge the stenotic vessel to facilitate the implantation of a valve stent. Moreover, balloon post-dilatation can achieve even better attachment of the aortic valve leaflets and hence even better therapeutic outcomes.

SUMMARY

Technical Problem

Nevertheless, since patients with severe calcified aortic stenosis tend to have a heavily calcified aortic valve, valve balloons must possess high puncture resistance in order to be not pierced by the calcified lesion in surgery. In addition, balloons used for the aortic valve must have a relatively large size (with a diameter in the range of from 8.0 mm to 50.0 mm). Such a bulky size means considerable compliance, which may possibly tear the valve due to over-expanded during the surgery, or bring damages to the structure of the valve stent due to post-dilatation towards the valve stent. However, existing valve balloons do not overcome these problems.

The inventors have found that existing valve balloons are made of a single nylon material having a high specification. Limited by this material factor, existing valve balloons have a relatively low puncture resistance but a relatively high compliance.

Technical Solution

An object of present application is to provide a balloon dilatation catheter, a balloon and a method of fabrication thereof for overcoming the problems that the existing valve balloons have a relatively low puncture resistance but a relatively high compliance.

To solve the above technical problem, present application provides a balloon which is made of a blend of at least two selected from the group consisting of L25, TR55, TR90 and TR70.

Optionally, the balloon is made of a blend of L25 and TR55, or a blend of L25 and TR90, a blend of L25, TR55 and TR90, or a blend of L25 and TR70.

Optionally, the balloon is made of a blend of L25 and TR55 with a weight ratio of L25 to TR55 ranging from 9:1 to 7:3, or a blend of L25 and TR90 with a weight ratio of L25 to TR90 ranging from 9:1 to 6:4, or a blend of L25, TR55 and TR90 with a weight percentage of TR90 of 10% and a weight ratio of L25 to TR55 ranging from 7:2 to 5:4, or a blend of L25 and TR70 with a weight ratio of L25 to TR70 ranging from 9:1 to 7:3.

Optionally, the balloon is made of a blend of L25 and TR55 with a weight ratio of L25 to TR55 of 8:2, or a blend of L25 and TR90 with a weight ratio of L25 to TR90 of 7:3 or 8:2, or a blend of L25, TR55 and TR90 with an L25:TR55:TR90 weight ratio of 6:3:1, or a blend of L25 and TR70 with a weight ratio of L25 to TR70 of 9:1.

Optionally, the balloon has a hollow multi-layer structure consisting of radially stacked layers of the same thickness and material.

Optionally, the multi-layer structure is a bi-layer structure or a tri-layer structure.

Optionally, the balloon has a dilated configuration, in which the balloon has a diameter ranging from 8 mm to 28 mm and a length ranging from 20 mm to 60 mm, and a compressed configuration.

Optionally, the balloon has a diameter of 8 mm, 18 mm, 20 mm, 26 mm or 28 mm in the dilated configuration.

Optionally, the balloon has a length of 20 mm, 30 mm, 40 mm, 50 mm or 60 mm.

To solve the above problem, present application also provides a balloon dilatation catheter comprising the balloon as defined above, an inner tube and an outer tube, the inner tube being inserted in the outer tube. The segment of the inner tube at a distal end of the inner tube extending out of the outer tube is sleeved with the balloon. The balloon has a distal end attached to the distal end of the inner tube, and a proximal end attached to both a distal end of the outer tube and the inner tube.

To solve the above problem, present application also provides a method for manufacturing the balloon as defined above, which comprises:

providing a hollow tube made of a blend of nylon materials; and filling the hollow tube with nitrogen, and heating, axial stretching, shaping and cooling the hollow tube in a molding chamber of a balloon-forming mold, so as to obtain the balloon.

Optionally, the hollow tube is extruded from an extruder.

Optionally, the step of filling the hollow tube with nitrogen, and heating, axial stretching, shaping and cooling the hollow tube in a molding chamber of a balloon-forming mold comprises:

closing one end of the hollow tube and introducing nitrogen from the other end of the hollow tube;

heating and axially stretching the hollow tube to manufacture a main body of the balloon;

axially stretching the main body of the balloon to manufacture an initial structure of the balloon, the initial structure of the balloon comprising a middle section, two balloon tapered sections and two balloon catheter sections, the two balloon tapered sections located at opposing ends of the middle section respectively, each balloon catheter section located at an end of a corresponding balloon tapered section away from the middle section; and shaping and cooling the initial structure of the balloon to obtain the balloon.

Optionally, the blend of nylon materials is a blend of L25 and TR55 with a weight ratio of L25 to TR55 ranging from 9:1 to 7:3; and the nitrogen is introduced into the hollow tube at a pressure ranging from 8 atm to 12 atm, and the hollow tube is heated to a temperature of from 100° C. to 120° C., and the step of shaping and cooling the initial structure of the balloon comprises: heating the initial structure of the balloon to a temperature of from 125° C. to 135° C., and pressurizing the initial structure of the balloon to a pressure of 10 atm; shaping the initial structure of the balloon for 10-14 s; and cooling the initial structure of the balloon with circulating water.

Optionally, the blend of nylon materials is a blend of L25 and TR90 with a weight ratio of L25 to TR90 ranging from 9:1 to 6:4, and the nitrogen is introduced into the hollow tube at a pressure ranging from 9.5 atm to 15.5 atm, and the hollow tube is heated to a temperature of from 100° C. to 130° C., and the step of shaping and cooling the initial structure of the balloon comprises: heating the initial structure of the balloon to a temperature of from 130° C. to 150° C.; pressurizing the initial structure of the balloon to a pressure of from 10 atm to 16 atm; shaping the initial structure of the balloon for 20-60 s; and cooling the initial structure of the balloon with circulating water.

Optionally, the blend of nylon materials is a blend of L25, TR55 and TR90 with a weight percentage of TR90 of 10% and a weight ratio of L25 to TR55 ranging from 7:2 to 5:4, and the nitrogen is introduced into the hollow tube at a pressure ranging from 11.5 atm to 13.5 atm, and the hollow tube is heated to a temperature of from 100° C. to 120° C., and the step of shaping and cooling the initial structure of the balloon comprises: heating the initial structure of the balloon to a temperature of from 130° C. to 140° C.; pressurizing the initial structure of the balloon to a pressure of from 11 atm to 15 atm; shaping the initial structure of the balloon for 20-40 s; and cooling the initial structure of the balloon with circulating water.

Optionally, the blend of nylon materials is a blend of L25 and TR70 with a weight ratio of L25 to TR70 ranging from 9:1 to 7:3, and the nitrogen is introduced into the hollow tube at a pressure ranging from 21.5 atm to 25.5 atm, and the hollow tube is heated to a temperature of from 100° C. to 120° C., and the step of shaping and cooling the initial structure of the balloon comprises: heating the initial structure of the balloon to a temperature of from 130° C. to 140° C.; pressurizing the initial structure of the balloon to a pressure of from 22 atm to 26 atm; shaping the initial structure of the balloon for 20-40 s; and cooling the initial structure of the balloon with circulating water.

In summary, in the balloon dilatation catheter, balloon and preparation method thereof provided in present application, the balloon is made of a blend of at least two selected from the group consisting of L25, TR55, TR90 and TR70, which allows the balloon of present application to have a higher puncture resistance and a lower compliance compared with the balloon made of a single nylon material. Additionally, the balloon of the present application has preferably a hollow multi-layer structure, which allows the balloon of present application to have an improved puncture resistance and a decreased compliance compared with the balloon having a single-layer structure.

BRIEF DESCRIPTION OF THE DRAWINGS

One object of the present application is to provide a balloon dilatation catheter, a balloon and a preparation method thereof. Those of ordinary skilled in the art will appreciate that the accompanying drawings are provided to enhance understanding of the present application and do not limit the scope thereof in any sense, in which.

In the figures.

10, balloon; 101, balloon catheter section; 102, balloon tapered section; 103, middle section; 20, inner tube; 30, radiopaque member; 40, outer tube; 50, sheath; 61, fluid introduction connecting member; and 62, guidewire connecting member.

DETAILED DESCRIPTION

To make the objects, advantages and features of the present application more apparent, present application is described in detail in conjunction with the accompanying drawings and embodiments. It is noted that the figures are provided in a very simplified form not necessarily presented to scale, with their only intention to facilitate convenience and clarity in explaining the embodiments of present application. In addition, structures shown in the accompanying drawings are usually portions of actual structures. In particular, as the figures tend to have distinct emphases, they are often drawn in different scales.

As used herein and in the appended claims, the singular forms "a", "an", and "the" include plural forms unless the context clearly dictates otherwise. As used herein and in the appended claims, the term "or" is generally employed in its sense including "and/or" unless the content clearly dictates otherwise. The term "proximal end" generally refers to the end close to the operator, and the term "distal end" generally refers to the end close to the site of lesion in patient.

Figure 1:
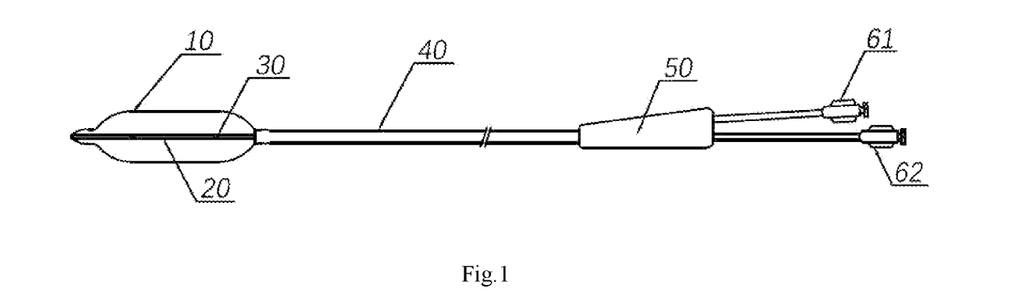
FIG. 1 is a schematic illustration of a balloon dilatation catheter according to an embodiment of the present application.
Figure 2:
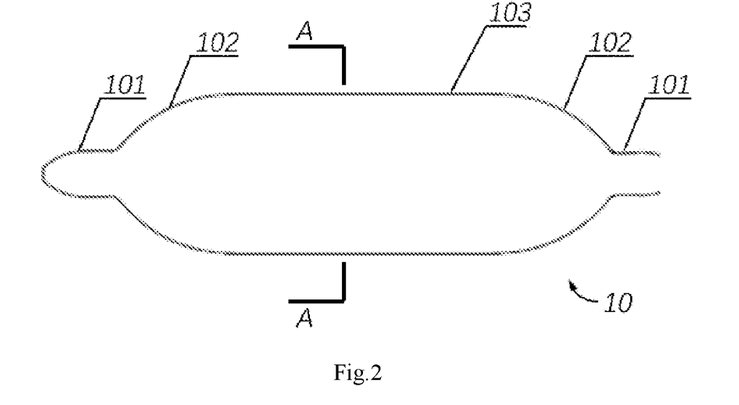
FIG. 2 is a schematic illustration of a balloon according to an embodiment of the present application.
Figure 3:
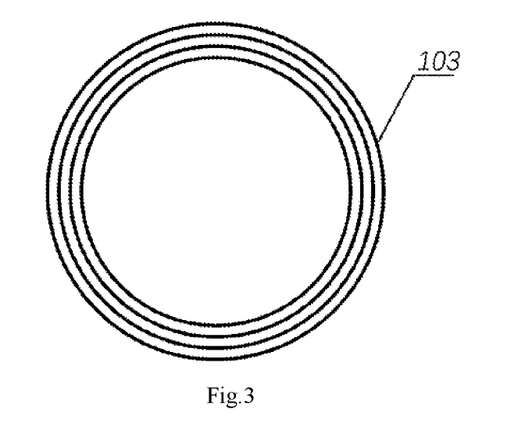
FIG. 3 shows a cross-sectional view of the balloon of FIG. 2 taken along line A-A.

Reference is now made to FIGS. 1 to 3. FIG. 1 schematically illustrates a balloon dilatation catheter according to an embodiment of the present application. FIG. 2 schematically illustrates a balloon according to an embodiment of the present application. FIG. 3 depicts a cross-sectional view of the balloon of FIG. 2 taken along line A-A.

As shown in FIG. 1, present application provides the balloon dilatation catheter including a balloon 10, an inner tube 20 and an outer tube 40. A segment of the inner tube 20 extending out of the outer tube 40 is provided with a balloon 10. A distal end of the balloon 10 is attached to the said segment of the inner tube 20, and a proximal end of the balloon 10 is attached both to a distal end of the outer tube 40 and to the inner tube 20. The balloon 10 is made of a blend of at least two grades of a nylon material. Here, the nylon material is nylon 12 (PA12), scientifically called polylaurolactam, which specifically includes various grades, for example, TR55, TR70, TR90 and L25. Different grades of nylon 12 have different molecular structures and distinct aggregation states and thus exhibit different properties. For example, the balloon 10 may be made of a blend of L25 and TR55, or a blend of L25 and TR90, or a blend of L25, TR55 and TR90, or a blend of L25 and TR70. Compared with balloons made of a single grade of a nylon material, the balloons 10 made of at least two grades of a nylon material has significantly improved puncture resistance and reduced compliance.

In one embodiment, the balloon 10 is made of a blend of L25 and TR55 with a weight ratio of L25 to TR55 ranging from 9:1 to 7:3, with 8:2 being more preferred. TR55 provides a high glass transition temperature, extremely high dynamic strength, resistance to impact and resistance to stress cracking.

In another embodiment, the balloon 10 is made of a blend of L25 and TR90 with a weight ratio of L25 to TR90 ranging from 9:1 to 6:4, with 7:3 or 8:2 being more preferred. TR90 provides extremely high dynamic strength.

In a further embodiment, the balloon 10 is made of a blend of L25, TR55 and TR90, in which TR90 is present at a weight percentage of 10%, and a weight ratio of L25 to TR55 ranges from 7:2 to 5:4. More preferably, an L25:TR55:TR90 weight ratio is 6:3:1.

In a further embodiment, the balloon 10 is made of a blend of L25 and TR70 with a weight ratio of L25 to TR70 ranging from 9:1 to 7:3, with 9:1 being more preferred. TR70 provides a high glass transition temperature.

The inventors have found that, compared to the balloons made of a single grade of a nylon material, the balloon 10 made of a blend of two or more of L25, TR55, TR70 and TR90 with an appropriate ratio of components has a higher puncture resistance and a lower compliance.

The balloon 10 has a middle section 103, two balloon tapered sections 102 and two balloon catheter sections 101. The two balloon tapered sections 102 are respectively located at opposing ends of the middle section 103, and each balloon catheter sections 101 is located at the end of the corresponding balloon tapered sections 102 away from the middle section 103. The distal one of the two balloon catheter sections 101 has its distal end sealed and attached to the distal end of the inner tube 20. The proximal one of the two balloon catheter sections 101 has its proximal end open and attached both to the distal end of the outer tube 40 and to the inner tube 20. Preferably, the inner tube 20 is configured coaxially with respect to the balloon 10.

Further, the balloon dilatation catheter also includes a radiopaque member 30, a sheath 50, a fluid introduction connecting member 61 and guidewire connecting member 62. The radiopaque member 30 is made of a radiopaque material, for example a platinum-iridium alloy that is opaque to X-rays, and is configured to monitor the position of the balloon 10 through a display screen by an X-ray fluoroscopy. The radiopaque member 30 may be arranged on said segment of the inner tube 20, particularly arranged on the inner tube 20 by crimping. The fluid introduction connecting member 61 and the guidewire connecting member 62 each have an end attached to a proximal end of the outer tube 40. The fluid introduction connecting member 61 may be in the form of a joint for deflating/inflating the balloon so that a contrast fluid can be injected into the balloon to dilate the balloon. The guidewire connecting member 62 may be so configured as to allow a guidewire to pass therethrough. The sheath 50 may be sleeved over a portion of the outer tube 40 attaching with the fluid introduction connecting member 61 and the guidewire connecting member 62 in order to protect the connection between the outer tube 40, the fluid introduction connecting member 61 and the guidewire connecting member 62 from being damaged and resulting in detachment.

Furthermore, the balloon dilatation catheter may be fabricated in the following manner.

In step S1, the balloon 10 is heated for 10 minutes and then the proximal end of the balloon 10 is attached to the distal end of the outer tube 40 by thermal blow molding.

In step S2, part of the inner tube 20 is inserted into the balloon 10, and the distal end of the balloon 10 is then attached to the inner tube 20 by thermal blow molding.

In step S3, the balloon 10 is folded into a five swing configuration and a fluid introduction inlet is formed in the outer tube 40.

In step S4, the fluid introduction connecting member 61 and the guidewire connecting member 62 are bonded to the outer tube 40 using a medical-grade glue.

In step S5, the sheath 50 is sleeved over a portion of the outer tube 40 away from the fluid introduction connecting member 61 and the guidewire connecting member 62.

Preferably, the balloon 10 has a hollow multi-layer structure consisting of radially stacked layers, each layer having the same thickness and made of the same material. More preferably, the balloon 10 has a hollow bi- or tri-layer structure. Compared with a single-layer structure, such a multi-layer structure allows further increasing puncture resistance of balloons and reducing compliance of balloons. The balloon 10 may have a dilated configuration and a compressed configuration and have different diameters in these configurations. The balloon 10 may be inflated to assume the dilated configuration in which the balloon 10 has a diameter preferably in the range of from 8 mm to 28 mm and a length preferably in the range of from 20 mm to 60 mm.

Benefits of the balloon 10 of the present application will be further described below with reference to the blending schemes of the nylon material as discussed above, together with experimental data and results, in order to further highlight features and advantages of the above various embodiments.

Embodiment 1

The balloon 10 in this embodiment is made of a blend of L25 and TR55 with a weight ratio of L25 to TR55 ranging from 9:1 to 7:3, with 8:2 being more preferred. With reference to FIGS. 2 and 3, such a balloon 10 was made as follows.

In step 1, the blend of nylon materials was extruded from an extruder to form a hollow tube, which was then placed into a molding chamber of a balloon forming mold. Herein, the blend of nylon materials is a blend of L25 and TR55. Preferably, the hollow tube has a tri-layer structure, and the balloon forming mold has a length preferably ranging from 47.8 mm to 50.6 mm.

In step 2, the hollow tube was closed at one end, and nitrogen was introduced into the hollow tube from the other end at a pressure of 8-12 atm.

In step 3, the hollow tube was heated to 100-120° C., and a tension between 200 N and 300 N was applied to both ends of the hollow tube to axially stretch the hollow tube 30-40 mm at a speed of 50-90 mm/s, thereby forming a main body of the balloon which is a diametrically constant tube.

In step 4, the main body of the balloon was further axially stretched 3-7 mm, thereby forming an initial structure of the balloon. The initial structure includes a middle section 103, two balloon tapered sections 102 and two balloon catheter sections 101. The two balloon tapered sections 102 are located at opposing ends of the middle section 103, respectively. Each of the two balloon catheter sections 101 is located at the end of a corresponding balloon tapered section 102 away from the middle section 103 (see FIG. 2).

In step 5, the initial structure of the balloon was heated to 125-135° C., pressurized to 10 atm, shaped for 10-14 s and cooled by introducing circulating water, thereby completing manufacture of the balloon 10.

As shown in FIG. 3, the balloon 10 obtained from the above steps has a hollow tri-layer structure, each layer having the same thickness and made of the same material. The balloon 10 in a dilated configuration has a diameter of 28 mm and a length of 40 mm. It is to be noted that diameter of the balloon 10 mentioned herein refers to maximum diameter of the balloon 10, that is, the outer diameter of the outmost layer of middle section of the balloon, rather than the diameter of balloon tapered section or the balloon catheter section. In addition, the length of the balloon 10 refers to a total axial length of the middle section and the two balloon tapered sections 102 exclusive of lengths of the two balloon catheter sections 101.

Subsequently, control balloons A1, B1 and C1 were further prepared according to the same steps. The control balloon A1 is made of a single material L25 and has a tri-layer structure having the same total thickness as the balloon 10 of this embodiment, each layer having a same thickness. The control balloon B1 is made of a L25/TR55 blend with the same components ratio as used in this embodiment but has a single-layer structure, thickness of which equals to the total thickness of the balloon 10 of this embodiment. The control balloon C1 is made of a single material L25 and has a single-layer structure, the thickness of which equals to the total thickness of the balloon 10 of this embodiment. Each of the control balloons A1, B1 and C1 had the same dimensions as the balloon 10 of this embodiment. Each of the control balloons A1, B1 and C1 is made in a similar manner, as the balloon 10 of this embodiment, and reference can be made to the above method for more details. Repeated description is omitted herein.

The balloon 10 provided in this embodiment and the control balloons A1, B1 and C1 were then tested for their puncture resistance and compliance.

A puncture resistance test for each balloon includes the steps of:

(A1) immersing the balloon in water bath at 37° C. for 2 minutes;

(A2) fixing a puncture needle vertically to a fixture on a tester;

(A3) adjusting the position of the fixture so that the puncture needle is aligned with the balloon arranged on the fixture;

(A4) inflating the balloon on the fixture to a rated burst pressure; and (A5) activating a testing program to perform test and recording puncture resistance readings on the tester.

In general, for the above mentioned test method, a balloon that can withstand a puncture force greater than 10 N will be considered to have a high puncture resistance. Higher puncture resistance means higher surgical reliability.

The compliance test for each balloon includes the steps of:

(B1) inflating the balloon to a nominal pressure Pn and measuring its nominal diameter Dn;

(B2) inflating the balloon to a rated burst pressure Prbp and measuring its burst diameter Drbp; and (B3) calculating a value of the balloon's compliance as:

$$\frac{Drbp - Dn}{Prbp - Pn}$$

In general, for a relatively large balloon (with a diameter of 8 mm or more), the greater the diameter is, the higher the compliance will be. Therefore, the criterion for determining whether such a balloon is a low-compliance one depends on the diameter of the balloon. A balloon with a diameter in the range of 8-14 mm can be considered as a low-compliance balloon if its calculated value of compliance is ≤0.1. For a balloon with a diameter in the range of 14-20 mm, the criterion can be a calculated value of compliance ≤0.8. For a balloon with a diameter in the range of 20-28 mm, the criterion can be a calculated value of compliance ≤1.5. Lower compliance means higher surgical reliability.

The related experimental data are summarized in Table 1.

TABLE 1

Puncture Resistance and Compliance of Balloons

|  | Puncture Resistance (N) | Compliance (mm/atm) |
| --- | --- | --- |
| Balloon 10 of present embodiment | 11.24 | 0.855 |
| Control Balloon A1 | 8.15 | 1.213 |
| Control Balloon B1 | 9.90 | 1.140 |
| Control Balloon C1 | 7.22 | 1.503 |

It can be seen from Table 1, the puncture resistance and compliance of the balloon 10 provided in present embodiment significantly better than that of the control balloons A1, B1 and C1.

The balloon 10 in this embodiment and the control balloon A1 have the same dimensions and the same tri-layer structures. The only difference between them is that the balloon 10 in this embodiment is made of a blend of L25 and TR55, while the control balloon A1 is made of only L25. Therefore, it can be concluded that the balloon made of L25/TR55 blend has a higher puncture resistance and a lower compliance when compared with the balloon made of a single material.

Moreover, the balloon 10 in this embodiment and the control balloon B1 are made of the same material, and have the same dimensions. The only difference between them is the number of layers in structure, that is, the balloon 10 in this embodiment has a tri-layer structure while the control balloon B1 has a single-layer structure. Therefore, it can be concluded that the balloon with a tri-layer structure has a higher puncture resistance and a lower compliance when compared with the balloon with a single-layer structure.

Comparisons made between the control balloons A1, B1 and C1 further reveal that an increase in puncture resistance and a reduction in compliance can be obtained either by using the L25/TR55 blend in place of the single material or by adopting the tri-layer structure in lieu of the single-layer structure.

Compared with the control balloon C1, the balloon 10 provided in this embodiment is modified in terms of both material and structure, and as demonstrated by the experimental results, using both the L25/TR55 blend and tri-layer structure allows raising puncture resistance of the balloon to a large extent and lowering compliance of the balloon distinctly.

Embodiment 2

The balloon 10 in this embodiment is made of a blend of L25 and TR90 with a weight ratio of L25 to TR90 between 9:1 and 6:4, with 7:3 being more preferred. Specifically, such a balloon 10 was made as follows.

In step 1, the blend of nylon materials was extruded from an extruder to form a hollow tube, which was then placed into a molding chamber of a balloon forming mould. Herein, the blend of nylon materials is a blend of L25 and TR90. Preferably, the hollow tube has a bi-layer structure, and the balloon forming mould has a length preferably ranging from 39.5 mm to 41.5 mm.

In step 2, the hollow tube was closed at one end, and nitrogen was introduced into the hollow tube from the other end at a pressure of 9.5-11.5 atm.

In step 3, the hollow tube was heated to 110-130° C., and a tension between 200 N and 300 N was applied to both ends of the hollow tube to axially stretch the hollow tube 20-30 mm at a speed of 80-120 mm/s, thereby forming a main body of the balloon which is a diametrically constant tube.

In step 4, the main body of the balloon was further axially stretched 5-10 mm, thereby forming an initial structure of the balloon. The initial structure includes a middle section 103, two balloon tapered sections 102 and two balloon catheter sections 101. The two balloon tapered sections 102 are located at opposing ends of the middle section 103, respectively. Each of the two balloon catheter sections 101 is located at the end of a corresponding balloon tapered section 102 away from the middle section 103.

In step 5, the initial structure of the balloon was heated to 140-150° C., pressurized to 10-14 atm, shaped for 40-60 s and cooled by introducing circulating water, thereby completing manufacture of the balloon 10.

The balloon 10 manufactured by the above steps has a hollow bi-layer structure consisting of two radially stacked layers of the same thickness and the same material. Besides, the balloon 10 in the dilated configuration has a diameter of 26 mm and a length of 30 mm. Here, the diameter and length of the balloon in this embodiment are defined in the same way as Embodiment 1.

Subsequently, control balloons A2, B2 and C2 were further prepared according to the same steps. The control balloon A2 is made of a single material L25 and has a bi-layer structure having the same total thickness as the balloon 10 having a bi-layer structure provided in this embodiment, each layer having a same thickness. The control balloon B2 is made of a L25/TR90 blend with the same components ratio as used in this embodiment but has a single-layer structure, thickness of which equals to the total thickness of the balloon 10 having a bi-layer structure provided in this embodiment. The control balloon C2 is made of a single material L25 and has a single-layer structure, the thickness of which equals to the total thickness of the balloon 10 having a bi-layer structure provided in this embodiment. Each of the control balloons A2, B2 and C2 had the same dimensions as the balloon 10 provided in this embodiment. Each of the control balloons A2, B2 and C2 is made in a similar manner, as the balloon 10 of this embodiment, and reference can be made to the above method for more details.

The balloon 10 provided in this embodiment and the control balloons A2, B2 and C2 were then tested for their puncture resistance and compliance. Reference can be made to Embodiment 1 for details in the test methods, which will not be described again here for the sake of brevity.

The related experimental data are summarized in Table 2.

TABLE 2

Puncture Resistance and Compliance of Balloons

| | Puncture Resistance (N) | Compliance (mm/atm) |
| --- | --- | --- |
| Balloon 10 of present embodiment | 13.78 | 0.450 |
| Control Balloon A2 | 9.12 | 0.680 |
| Control Balloon B2 | 9.60 | 0.655 |
| Control Balloon C2 | 7.31 | 0.814 |

As seen from Table 2, the balloon 10 provided in present Embodiment obviously surpasses the control balloons A2, B2 and C2 in terms of puncture resistance and compliance. The balloon 10 in this embodiment and the control balloon A2 have the same dimensions and the same bi-layer structures. The only difference between them is that the balloon 10 in this embodiment is made of a blend of L25 and TR90, while the control balloon A2 is made of only L25. Therefore, it can be concluded that the balloon made of L25/TR90 blend has a higher puncture resistance and a lower compliance when compared with the balloon made of a single material. Moreover, the balloon 10 in this embodiment and the control balloon B2 are made of the same material, and have the same dimensions. The only difference between them is the number of layers in structure, that is, the balloon 10 in this embodiment has a bi-layer structure while the control balloon B2 has a single-layer structure. Therefore, it can be concluded that the balloon with a bi-layer structure has a higher puncture resistance and a lower compliance when compared with the balloon with a single-layer structure. Comparisons made between the control balloons A2, B2 and C2 further reveal that an increase in puncture resistance and a reduction in compliance can be obtained either by using the L25/TR90 blend in place of the single material or by adopting the bi-layer structure in lieu of the single-layer structure. Compared with the control balloon C2, the balloon 10 provided in this embodiment is modified in terms of both material and structure, and as demonstrated by the experimental results, using both the L25/TR90 blend and bi-layer structure allows raising puncture resistance of the balloon to a large extent as well as lowering compliance of the balloon distinctly.

Embodiment 3

The balloon 10 in this embodiment is made of a blend of L25, TR55 and TR90 with a weight percentage of TR90 of 10% and a weight ratio of L25 to TR55 ranging from 7:2 to 5:4. Preferably, a L25:TR55:TR90 weight ratio is 6:3:1.

Specifically, the balloon 10 was made as follows.

In step 1, the blend of nylon materials was extruded from an extruder to form a hollow tube, which was then placed into a molding chamber of a balloon forming mould. Herein, the blend of nylon materials is a blend of L25, TR55 and TR90. Preferably, the hollow tube has a tri-layer structure, and the balloon forming mould has a length preferably ranging from 57.5 mm to 59.5 mm.

In step 2, the hollow tube was closed at one end, and nitrogen was introduced therein from the other end at a pressure of 11.5-13.5 atm.

In step 3, the hollow tube was heated to 100-120° C., and a tension between 160 N and 220 N was applied to both ends of the hollow tube to axially stretch the hollow tube 30-50 mm at a speed of 80-120 mm/s, thereby forming a main body of the balloon which is a diametrically constant tube.

In step 4, the main body was further axially stretched 10-15 mm, thereby forming an initial structure of the balloon. The initial structure includes a middle section 103, two balloon tapered sections 102 and two balloon catheter sections 101. The two balloon tapered sections 102 are located at opposing ends of the middle section 103, respectively. Each of the two balloon catheter sections 101 is located at the end of a corresponding balloon tapered section 102 away from the middle section 103.

In step 5, the initial form was heated to 130-140° C. and pressurized to 11-15 atm, shaped for 20-40 s and cooled by introducing circulating water, thereby completing manufacture of the balloon 10.

The balloon 10 manufactured by the above steps has a hollow tri-layer structure consisting of three radially stacked layers of the same thickness and the same material. Besides, the balloon 10 in the dilated configuration has a diameter of 20 mm and a length of 50 mm. Here, the diameter and length of the balloon in this embodiment are defined in the same way as Embodiment 1.

Subsequently, control balloons A3, B3 and C3 were further prepared according to the same steps. The control balloon A3 is made of a single material L25 and has a tri-layer structure having the same total thickness as the balloon 10 having a tri-layer structure provided in this embodiment, each layer having a same thickness. The control balloon B3 is made of a L25, TR55 and TR90 blend with the same components ratio as used in this embodiment but has a single-layer structure, thickness of which equals to the total thickness of the balloon 10 having a tri-layer structure provided in this embodiment. The control balloon C3 is made of a single material L25 and has a single-layer structure, the thickness of which equals to the total thickness of the balloon 10 having a tri-layer structure provided in this embodiment. Each of the control balloons A3, B3 and C3 had the same dimensions as the balloon 10 provided in this embodiment. Each of the control balloons A3, B3 and C3 is made in a similar manner, as the balloon 10 of this embodiment, and reference can be made to the above method for more details.

The balloon 10 provided in this embodiment and the control balloons A3, B3 and C3 were then tested for their puncture resistance and compliance. Reference can be made to Embodiment 1 for details in the test methods, which will not be described again here for the sake of brevity.

The related experimental data are summarized in Table 3.

TABLE 3

Puncture Resistance and Compliance of Balloons

| | Puncture Resistance (N) | Compliance (mm/atm) |
|---|---|---|
| Balloon 10 of present embodiment | 12.95 | 0.340 |
| Control Balloon A3 | 7.81 | 0.515 |
| Control Balloon B3 | 8.20 | 0.405 |
| Control Balloon C3 | 5.59 | 0.557 |

As seen from Table 3, the balloon 10 provided in present Embodiment obviously surpasses the control balloons A3, B3 and C3 in terms of puncture resistance and compliance. The balloon 10 in this embodiment and the control balloon A3 have the same dimensions and the same tri-layer structures. The only difference between them is that the balloon 10 in this embodiment is made of a blend of L25, TR55 and TR90, while the control balloon A3 is made of only L25. Therefore, it can be concluded that the balloon made of L25/TR55/TR90 blend has a higher puncture resistance and a lower compliance when compared with the balloon made of a single material. Moreover, the balloon 10 in this embodiment and the control balloon B3 are made of the same material, and have the same dimensions. The only difference between them is the number of layers in structure, that is, the balloon 10 in this embodiment has a tri-layer structure while the control balloon B3 has a single-layer structure. Therefore, it can be concluded that the balloon with a tri-layer structure has a higher puncture resistance and a lower compliance when compared with the balloon with a single-layer structure. Comparisons made between the control balloons A3, B3 and C3 further reveal that an increase in puncture resistance and a reduction in compliance can be obtained either by using the L25/TR55/TR90 blend in place of the single material or by adopting the tri-layer structure in lieu of the single-layer structure. Compared with the control balloon C3, the balloon 10 provided in this embodiment is modified in terms of both material and structure, and as demonstrated by the experimental results, using both the L25/TR55/TR90 blend and tri-layer structure allows raising puncture resistance of the balloon to a large extent as well as lowering compliance of the balloon distinctly.

Embodiment 4

The balloon 10 in this embodiment is made of a blend of L25 and TR90 with a weight ratio of L25 to TR90 ranging from 9:1 to 7:3, with 8:2 being more preferred.

Specifically, such a balloon 10 was made as follows.

In step 1, the blend of nylon materials was extruded from an extruder to form a hollow tube, which was then placed into a molding chamber of a balloon forming mould. Herein, the blend of nylon materials is a blend of L25 and TR90. Preferably, the hollow tube has a tri-layer structure, and the balloon forming mould has a length preferably ranging from 59.5 mm to 61.5 mm.

In step 2, the hollow tube was closed at one end, and nitrogen was introduced therein from the other end at a pressure of 12.5-15.5 atm.

In step 3, the hollow tube was heated to 100-120° C., and a tension between 160 N and 220 N was applied to both ends of the hollow tube to axially stretch the hollow tube 50-70 mm at a speed of 80-120 mm/s, thereby forming a main body of the balloon which is a diametrically constant tube.

In step 4, the main body of the balloon was further axially stretched 10-15 mm, thereby forming an initial structure of the balloon. The initial structure includes a middle section 103, two balloon tapered sections 102 and two balloon catheter sections 101. The two balloon tapered sections 102 are located at opposing ends of the middle section 103, respectively. Each of the two balloon catheter sections 101 is located at the end of a corresponding balloon tapered section 102 away from the middle section 103.

In step 5, the initial structure of the balloon was heated to 130-140° C., pressurized to 12-16 atm, shaped for 20-40 s and cooled by introducing circulating water, thereby completing manufacture of the balloon 10.

The balloon 10 manufactured by the above steps has a hollow tri-layer structure consisting of three radially stacked layers of the same thickness and the same material. Besides, the balloon 10 in the dilated configuration has a diameter of 18 mm and a length of 60 mm. Here, the diameter and length of the balloon in this embodiment are defined in the same way as Embodiment 1.

Subsequently, control balloons A4, B4 and C4 were further prepared according to the same steps. The control balloon A4 is made of a single material L25 and has a tri-layer structure having the same total thickness as the balloon 10 having a tri-layer structure provided in this embodiment, each layer having a same thickness. The control balloon B4 is made of a L25/TR90 blend with the same components ratio as used in this embodiment but has a single-layer structure, thickness of which equals to the total thickness of the balloon 10 having a tri-layer structure provided in this embodiment. The control balloon C4 is made of a single material L25 and has a single-layer structure, the thickness of which equals to the total thickness of the balloon 10 having a tri-layer structure provided in this embodiment. Each of the control balloons A4, B4 and C4 had the same dimensions as the balloon 10 provided in this embodiment. Each of the control balloons A4, B4 and C4 is made in a similar manner, as the balloon 10 of this embodiment, and reference can be made to the above method for more details.

The balloon 10 provided in this embodiment and the control balloons A4, B4 and C4 were then tested for their puncture resistance and compliance. Reference can be made to Embodiment 1 for details in the test methods, which will not be described again here for the sake of brevity.

The related experimental data are summarized in Table 4.

TABLE 4

Puncture Resistance and Compliance of Balloons

| | Puncture Resistance (N) | Compliance (mm/atm) |
|---|---|---|
| Balloon 10 of present embodiment | 12.89 | 0.305 |
| Control Balloon A4 | 8.35 | 0.450 |
| Control Balloon B4 | 8.50 | 0.424 |
| Control Balloon C4 | 6.50 | 0.513 |

As seen from Table 4, the balloon 10 surpasses the control balloons A4, B4 and C4 in terms of puncture resistance and compliance. The balloon 10 in this embodiment and the control balloon A4 have the same dimensions and the same tri-layer structures. The only difference between them is that the balloon 10 in this embodiment is made of a blend of L25 and TR90, while the control balloon A4 is made of only L25. Therefore, it can be concluded that the balloon made of L25/TR90 blend has a higher puncture resistance and a lower compliance when compared with the balloon made of a single material. Moreover, the balloon 10 in this embodiment and the control balloon B4 are made of the same material, and have the same dimensions. The only difference between them is the number of layers in structure, that is, the balloon 10 in this embodiment has a tri-layer structure while the control balloon B4 has a single-layer structure. Therefore, it can be concluded that the balloon with a tri-layer structure has a higher puncture resistance and a lower compliance when compared with the balloon with a single-layer structure. Comparisons made between the control balloons A4, B4 and C4 further reveal that an increase in puncture resistance and a reduction in compliance can be obtained either by using the L25/TR90 blend in place of the single material or by adopting the tri-layer structure in lieu of the single-layer structure. Compared with the control balloon C4, the balloon 10 provided in this embodiment is modified in terms of both material and structure, and as demonstrated by the experimental results, using both the L25/TR90 blend and tri-layer structure allows raising puncture resistance of the balloon to a large extent as well as lowering compliance of the balloon distinctly.

Embodiment 5

The balloon 10 in this embodiment is made a blend of L25 and TR70 with a weight ratio of L25 to TR70 ranging from 9:1 to 7:3, with 9:1 being more preferred.

Specifically, such a balloon 10 was made as follows.

In step 1, the blend of nylon materials was extruded from an extruder to form a hollow tube, which was then placed into a molding chamber of a balloon forming mould. Herein, the blend of nylon materials is a blend of L25 and TR70. Preferably, the hollow tube has a tri-layer structure, and the balloon forming mould has a length preferably ranging from 19.5 mm to 21.5 mm.

In step 2, the hollow tube was closed at one end, and nitrogen was introduced therein from the other end at a pressure of 21.5-25.5 atm.

In step 3, the hollow tube was heated to 100-120° C., and a tension between 160 N and 220 N was applied to both ends of the hollow tube to axially stretch the hollow tube 10-20 mm at a speed of 80-120 mm/s, thereby forming a main body of the balloon which is a diametrically constant tube.

In step 4, the main body of the balloon was further axially stretched 3-8 mm, thereby forming an initial structure of the balloon. The initial structure includes a middle section 103, two balloon tapered sections 102 and two balloon catheter sections 101. The two balloon tapered sections 102 are located at opposing ends of the middle section 103, respectively. Each of the two balloon catheter sections 101 is located at the end of a corresponding balloon tapered section 102 away from the middle section 103.

In step 5, the initial structure of the balloon was heated to 130-140° C., pressurized to 22-26 atm, shaped for 20-40 s and cooled by introducing circulating water, thereby completing manufacture of the balloon 10.

The balloon 10 manufactured by the above steps has a hollow tri-layer structure consisting of three radially stacked layers of the same thickness and the same material. Besides, the balloon 10 in the dilated configuration has a diameter of 8 mm and a length of 20 mm. Here, the diameter and length of the balloon in this embodiment are defined in the same way as Embodiment 1.

Subsequently, control balloons A5, B5 and C5 were further prepared according to the same steps. The control balloon A5 is made of a single material L25 and has a tri-layer structure having the same total thickness as the balloon 10 having a tri-layer structure provided in this embodiment, each layer having a same thickness. The control balloon B5 is made of a L25/TR70 blend with the same components ratio as used in this embodiment but has a single-layer structure, thickness of which equals to the total thickness of the balloon 10 having a tri-layer structure provided in this embodiment. The control balloon C5 is made of a single material L25 and has a single-layer structure, the thickness of which equals to the total thickness of the balloon 10 having a tri-layer structure provided in this embodiment. Each of the control balloons A5, B5 and C5 had the same dimensions as the balloon 10 provided in this embodiment. Each of the control balloons A5, B5 and C5 is made in a similar manner, as the balloon 10 of this embodiment, and reference can be made to the above method for more details.

The balloon 10 provided in this embodiment and the control balloons A5, B5 and C5 were then tested for their puncture resistance and compliance. Reference can be made to Embodiment 1 for details in the test methods, which will not be described again here for the sake of brevity.

The related experimental data are summarized in Table 5.

TABLE 5

Puncture Resistance and Compliance of Balloons

| | Puncture Resistance (N) | Compliance (mm/atm) |
|---|---|---|
| Balloon 10 of present embodiment | 10.56 | 0.155 |
| Control Balloon A5 | 6.37 | 0.277 |
| Control Balloon B5 | 7.40 | 0.225 |
| Control Balloon C5 | 5.50 | 0.310 |

As seen from Table 5, the balloon 10 provided in present Embodiment obviously surpasses the control balloons A5, B5 and C5 in terms of puncture resistance and compliance. The balloon 10 in this embodiment and the control balloon A5 have the same dimensions and the same tri-layer structures. The only difference between them is that the balloon 10 in this embodiment is made of a blend of L25 and TR70, while the control balloon A2 is made of only L25. Therefore, it can be concluded that the balloon made of L25/TR70 blend has a higher puncture resistance and a lower compliance when compared with the balloon made of a single material. Moreover, the balloon 10 in this embodiment and the control balloon B5 are made of the same material, and have the same dimensions. The only difference between them is the number of layers in structure, that is, the balloon 10 in this embodiment has a tri-layer structure while the control balloon B2 has a single-layer structure. Therefore, it can be concluded that the balloon with a tri-layer structure has a higher puncture resistance and a lower compliance when compared with the balloon with a single-layer structure. Comparisons made between the control balloons A5, B5 and C5 further reveal that an increase in puncture resistance and a reduction in compliance can be obtained either by using the L25/TR70 blend in place of the single material or by adopting the tri-layer structure in lieu of the single-layer structure. Compared with the control balloon C5, the balloon 10 provided in this embodiment is modified in terms of both material and structure, and as demonstrated by the experimental results, using both the L25/TR70 blend and tri-layer structure allows raising puncture resistance of the balloon to a large extent as well as lowering compliance of the balloon distinctly.

In summary, compared with the existing balloons made of a single grade of a nylon material, the balloons 10 according to embodiments of the present application made of a blend of at least two selected from the group consisting of L25, TR55, TR90 and TR70 have higher puncture resistances and lower compliances. Additionally, the balloon 10 of the present application has preferably a hollow multi-layer structure, which allows the balloon of present application to have an improved puncture resistance and a decreased compliance compared with the balloon having a single-layer structure.

The description presented above is merely a few preferred embodiments of the present application without limiting the scope thereof in any sense. Any change and modification made by those of ordinary skill in the art based on the above disclosure fall within the protection scope as defined by the appended claims.

What is claimed is:

1. A balloon, wherein the balloon is made of a blend of:
Nylon L25 and Nylon TR55 with a weight ratio of Nylon L25 to Nylon TR55 ranging from 9:1 to 7:3; or
   Nylon L25 and Nylon TR90 with a weight ratio of Nylon L25 to Nylon TR90 ranging from 9:1 to 6:4; or
   Nylon L25, Nylon TR55 and Nylon TR90, wherein the Nylon TR90 is present at a weight percentage of 10% and a weight ratio of Nylon L25 to Nylon TR55 ranges from 7:2 to 5:4; or
   Nylon L25 and Nylon TR70 with a weight ratio of Nylon L25 to Nylon TR70 ranging from 9:1 to 7:3,
   wherein the balloon has a hollow multi-layer structure consisting of radially stacked layers of the same thickness and material.

2. The balloon according to claim 1, wherein the balloon is made of a blend of:
Nylon L25 and Nylon TR55 with a weight ratio of Nylon L25 to Nylon TR55 of 8:2; or
Nylon L25 and Nylon TR90 with a weight ratio of Nylon L25 to Nylon TR90 of 7:3 or 8:2; or
Nylon L25, Nylon TR55 and Nylon TR90 with a Nylon L25:Nylon TR55:Nylon TR90 weight ratio of 6:3:1; or
Nylon L25 and Nylon TR70 with a weight ratio of Nylon L25 to Nylon TR70 of 9:1.

3. The balloon according to claim 1, wherein the multi-layer structure is a bi-layer structure or a tri-layer structure.

4. The balloon according to claim 1, wherein the balloon has a dilated configuration, in which the balloon has a diameter ranging from 8 mm to 28 mm and a length ranging from 20 mm to 60 mm, and a compressed configuration.

5. The balloon according to claim 4, wherein the balloon has a diameter of 8 mm, 18 mm, 20 mm, 26 mm or 28 mm in the dilated configuration.

6. The balloon according to claim 4, wherein the balloon has a length of 20 mm, 30 mm, 40 mm, 50 mm or 60 mm.

7. A balloon dilatation catheter, comprising the balloon according to claim 1, an inner tube and an outer tube, the inner tube being inserted in the outer tube, wherein the inner tube is inserted in the outer tube, and the balloon is sleeved on a distal segment of the inner tube extending out of the outer tube, and wherein the balloon has a distal end attached to a distal end of the inner tube, and a proximal end attached to a distal end of the outer tube.

8. A method of manufacturing the balloon according to claim 1, comprising:
providing a hollow tube made of a blend of nylon materials; and
filling the hollow tube with nitrogen, and heating, axial stretching, shaping and cooling the hollow tube in a molding chamber of a balloon-forming mold, so as to obtain the balloon.

9. The method of claim 8, wherein the hollow tube is extruded from an extruder.

10. The method of claim 8, wherein the step of filling the hollow tube with nitrogen, and heating, axial stretching, shaping and cooling the hollow tube in a molding chamber of a balloon-forming mold comprises:
closing one end of the hollow tube and introducing nitrogen from the other end of the hollow tube;
heating and axially stretching the hollow tube to manufacture a main body of the balloon;
axially stretching the main body of the balloon to manufacture an initial structure of the balloon, the initial structure of the balloon comprising a middle section, two balloon tapered sections and two balloon catheter sections, wherein the two balloon tapered sections are located at opposing ends of the middle section respectively, and each balloon catheter section is located at an end of a corresponding balloon tapered section away from the middle section; and
shaping and cooling the initial structure of the balloon to obtain the balloon.

11. The method of claim 10, wherein the blend of nylon materials is a blend of L25 and TR55 with a weight ratio of L25 to TR55 ranging from 9:1 to 7:3, and
wherein the nitrogen is introduced into the hollow tube at a pressure ranging from 8 atm to 12 atm, and the hollow tube is heated to a temperature of from 100° C. to 120° C., and wherein the step of shaping and cooling the initial structure of the balloon comprises: heating the initial structure of the balloon to a temperature of from 125° C. to 135° C., and pressurizing the initial structure of the balloon to a pressure of 10 atm; shaping the initial structure of the balloon for 10-14 s; and cooling the initial structure of the balloon with circulating water.

12. The method of claim 10, wherein the blend of nylon materials is a blend of L25 and TR90 with a weight ratio of L25 to TR90 ranging from 9:1 to 6:4, and wherein the nitrogen is introduced into the hollow tube at a pressure ranging from 9.5 atm to 15.5 atm, and the hollow tube is heated to a temperature of from 100° C. to 130° C., wherein the step of shaping and cooling the initial structure of the balloon comprises: heating the initial structure of the balloon to a temperature of from 130° C. to 150° C.; pressurizing the initial structure of the balloon to a pressure of from 10 atm to 16 atm; shaping the initial structure of the balloon for 20-60 s; and cooling the initial structure of the balloon with circulating water.

13. The method of claim 10, wherein the blend of nylon materials is a blend of L25, TR55 and TR90 with a weight percentage of TR90 of 10% and a weight ratio of L25 to TR55 ranging from 7:2 to 5:4, and wherein the nitrogen is introduced into the hollow tube at a pressure ranging from 11.5 atm to 13.5 atm, and the hollow tube is heated to a temperature of from 100° C. to 120° C., wherein the step of shaping and cooling the initial structure of the balloon comprises: heating the initial structure of the balloon to a temperature of from 130° C. to 140° C.; pressurizing the initial structure of the balloon to a pressure of from 11 atm to 15 atm; shaping the initial structure of the balloon for 20-40 s; and cooling the initial structure of the balloon with circulating water.

14. The method of claim 10, wherein the blend of nylon materials is a blend of L25 and TR70 with a weight ratio of L25 to TR70 ranging from 9:1 to 7:3, and wherein the nitrogen is introduced into the hollow tube at a pressure ranging from 21.5 atm to 25.5 atm, and the hollow tube is heated to a temperature of from 100° C. to 120° C., wherein the step of shaping and cooling the initial structure of the balloon comprises: heating the initial structure of the balloon to a temperature of from 130° C. to 140° C.; pressurizing the initial structure of the balloon to a pressure of from 22 atm to 26 atm; shaping the initial structure of the balloon for 20-40 s; and cooling the initial structure of the balloon with circulating water.

* * * * *